United States Patent
Rana et al.

(10) Patent No.: US 10,642,028 B2
(45) Date of Patent: May 5, 2020

(54) LENS POSITION ADJUSTMENT IN A WEARABLE DEVICE

(71) Applicant: Tobii AB, Danderyd (SE)

(72) Inventors: Pravin Rana, Danderyd (SE); Daniel Tornéus, Danderyd (SE)

(73) Assignee: Tobii AB, Danderyd (SE)

( * ) Notice: Subject to any disclaimer, the term of this patent is extended or adjusted under 35 U.S.C. 154(b) by 0 days.

(21) Appl. No.: 15/893,014

(22) Filed: Feb. 9, 2018

(65) Prior Publication Data

US 2018/0246320 A1 Aug. 30, 2018

Related U.S. Application Data

(60) Provisional application No. 62/464,235, filed on Feb. 27, 2017.

(51) Int. Cl.
*G06T 7/70* (2017.01)
*G02B 26/08* (2006.01)
(Continued)

(52) U.S. Cl.
CPC .......... *G02B 26/0875* (2013.01); *A61B 3/112* (2013.01); *A61B 3/113* (2013.01);
(Continued)

(58) Field of Classification Search
CPC ............ G02B 26/0875; G02B 27/0093; A61B 5/6803; A61B 5/1103; A61B 5/163;
(Continued)

(56) References Cited

U.S. PATENT DOCUMENTS 6,299,307 B1 10/2001 Oltean
6,322,216 B1* 11/2001 Yee .................. A61B 3/113
351/210
(Continued)

FOREIGN PATENT DOCUMENTS

EP 1 700 567 A1 9/2006
JP 2001 225666 A 8/2001
WO 2016/077601 A1 5/2016

OTHER PUBLICATIONS

U.S. Appl. No. 15/893,340, filed Feb. 9, 2018, Non-Final Rejection dated Jul. 24, 2018, all pages.

*Primary Examiner* — Amit Chatly
(74) *Attorney, Agent, or Firm* — Samuel Yamron

(57) ABSTRACT

A system for adjusting a position of a lens in a wearable device is provided. The system may include a wearable device and a processor. The wearable device may include a display, a lens movably disposed in front of the display, and an eye tracking device including an illuminator and an image sensor. The processor may receive data from the eye tracking device, and determine, based on the data, a first position of the eye of a user wearing the wearable device, where the position is relative to a second position which is fixed with respect to the lens. The processor may also be configured to determine a distance between the first position and the second position, and if the distance is greater than a first value, cause information to be presented to the user indicating that the lens should be moved to a more optimal position.

18 Claims, 12 Drawing Sheets

(51) Int. Cl.

| | | |
|---|---|---|
| *G06F 3/01* | (2006.01) | |
| *G06K 9/00* | (2006.01) | |
| *G02B 27/00* | (2006.01) | |
| *G06T 7/73* | (2017.01) | |
| *A61B 5/16* | (2006.01) | |
| *A61B 3/11* | (2006.01) | |
| *A61B 3/113* | (2006.01) | |
| *A61B 5/107* | (2006.01) | |
| *A61B 5/11* | (2006.01) | |
| *A61B 5/00* | (2006.01) | |

(52) U.S. Cl.
CPC .......... *A61B 5/1079* (2013.01); *A61B 5/1103* (2013.01); *A61B 5/163* (2017.08); *A61B 5/6803* (2013.01); *G02B 27/0093* (2013.01); *G06F 3/013* (2013.01); *G06K 9/00597* (2013.01); *G06K 9/00604* (2013.01); *G06T 7/70* (2017.01); *G06T 7/73* (2017.01); *G06T 2207/30201* (2013.01)

(58) Field of Classification Search
CPC ....... A61B 3/112; A61B 3/113; A61B 5/1079; G06T 7/70; G06T 7/73; G06T 2207/30201; G06K 9/00597; G06K 9/00604; G06F 3/013
See application file for complete search history.

(56) References Cited

U.S. PATENT DOCUMENTS

| | | |
|---|---|---|
| 6,459,446 B1 | 10/2002 | Harman |
| 6,702,809 B1 | 3/2004 | Knopp |
| 6,980,691 B2 | 12/2005 | Nesterov et al. |
| 7,415,126 B2 | 8/2008 | Breed |
| 7,809,160 B2 | 10/2010 | Vertegaal et al. |
| 8,315,440 B2 | 11/2012 | Cambier |
| 8,437,513 B1 | 5/2013 | Derakhshani |
| 8,824,779 B1 | 9/2014 | Smyth et al. |
| 8,902,070 B2 | 12/2014 | Kobetski et al. |
| 9,025,830 B2 | 5/2015 | Ma et al. |
| 2005/0007552 A1 | 1/2005 | Fergason et al. |
| 2014/0375540 A1* | 12/2014 | Ackerman ............... G06F 3/013 345/156 |
| 2017/0184847 A1* | 6/2017 | Petrov .................. G02B 27/017 |

* cited by examiner

LENS POSITION ADJUSTMENT IN A WEARABLE DEVICE

CROSS-REFERENCE TO RELATED APPLICATIONS

This application claims priority to, and the benefit of, U.S. Provisional Patent Application No. 62/464,235, filed Feb. 27, 2017, the entire contents of which are hereby incorporated by reference, for all purposes, as if fully set forth herein.

This application is also related to U.S. patent application Ser. No. 15/893,340, filed on a date concurrently herewith, the entire contents of which are hereby incorporated by reference, for all purposes, as if fully set forth herein.

BRIEF SUMMARY OF THE INVENTION

In one embodiment, a system for adjusting a position of a lens in a wearable device is provided. The system may include a wearable device and one or more processors. The wearable device may include a display, at least one lens movably disposed in front of the display, and an eye tracking device including at least one illuminator and at least on image sensor. The one or more processors may be configured to receive data from the eye tracking device, and determine, based at least on the data, a first position of at least one eye of a user wearing the wearable device, where the position is relative to a second position which is fixed with respect to the at least one lens. The one or more processors may also be configured to determine a distance between the first position and the second position, and if the distance is greater than a first value, cause information to be presented to the user indicating that the one or more lens should be moved to a more optimal position.

In another embodiment, a method for adjusting a position of a lens in a wearable device is provided. The method may include receiving data from an eye tracking device in a wearable device including a display and at least one lens movably disposed in front of the display. The method may also include receiving data from the eye tracking device. The method may further include determining, based at least on the data, a first position of at least one eye of a user wearing the wearable device, where the position is relative to a second position which is fixed with respect to the at least one lens. The method may additionally include determining a distance between the first position and the second position. The method may moreover include, if the distance is greater than a first value or less than a second value, causing information to be presented to the user indicating that the one or more lens should be moved to a more optimal position.

In another embodiment, a non-transitory machine readable medium is provided. The non-transitory machine readable medium may have instructions stored thereon for adjusting a position of a lens in a wearable device. The instructions may be executable by one or more processors to perform a method. The method may include receiving data from an eye tracking device in a wearable device including a display and at least one lens movably disposed in front of the display. The method may also include receiving data from the eye tracking device. The method may further include determining, based at least on the data, a first position of at least one eye of a user wearing the wearable device, where the position is relative to a second position which is fixed with respect to the at least one lens. The method may additionally include determining a distance between the first position and the second position. The method may moreover include, if the distance is greater than a first value or less than a second value, causing the at least one lens to be moved until the distance is less than the first value and greater than the second value.

In other embodiments, systems and methods for determining eye openness with an eye tracking device are provided. These embodiments may include determining, for at least a portion of pixels of an image sensor of an eye tracking device, during a first time period when an eye of a user is open, a first sum of intensity of the pixels. The embodiments may also include determining, for the at least portion of pixels of the image sensor of the eye tracking device, during a second time period when the eye of the user is closed, a second sum of intensity of the pixels. The embodiments may further include determining, for the at least portion of pixels of the image sensor of the eye tracking device, during a third time period, a third sum of intensity of the pixels. The embodiments may additionally include determining, with a processor, that upon the third sum exceeding a fourth sum of the first sum plus a threshold amount, that the eye of the user is closed, where the threshold amount is equal to a product of a threshold fraction and a difference between the first sum and the second sum.

In other embodiments, systems and methods for determining eye openness with an eye tracking device are provided. These embodiments may include activating a plurality of illuminators of an eye tracking device, where the plurality of illuminators are directed toward an eye of a user. The embodiments may also include determining, with an image sensor of an eye tracking device, how many reflections of activated illuminators are present on the eye of the user. The embodiments may further include determining, with at least one processor, based on less than a first predefined number of reflections being present, that the eye of the user is closed.

In other embodiments, systems and methods for determining eye openness with an eye tracking device are provided. These embodiments may include receiving, at one or more processors, an image of an eye of a user from an image sensor of an eye tracking device. The embodiments may also include determining, with the one or more processors, based on the image of the eye, a radius of the pupil. The embodiments may further include determining, with the one or more processors, based on the radius of the pupil, a total area of the pupil. The embodiments may additionally include determining, with the one or more processors, based on the image of the eye and the radius of the pupil, an amount of the total area of the pupil which is not obscured by either eyelid. The embodiments may moreover include determining, with the one or more processors, based on the amount of the total area of the pupil which is not obscured by the eyelid and the total area of the pupil, whether the eye of the user is closed.

BRIEF DESCRIPTION OF THE DRAWINGS

Embodiments of the present invention are described in conjunction with the appended figures.

Figure 1:
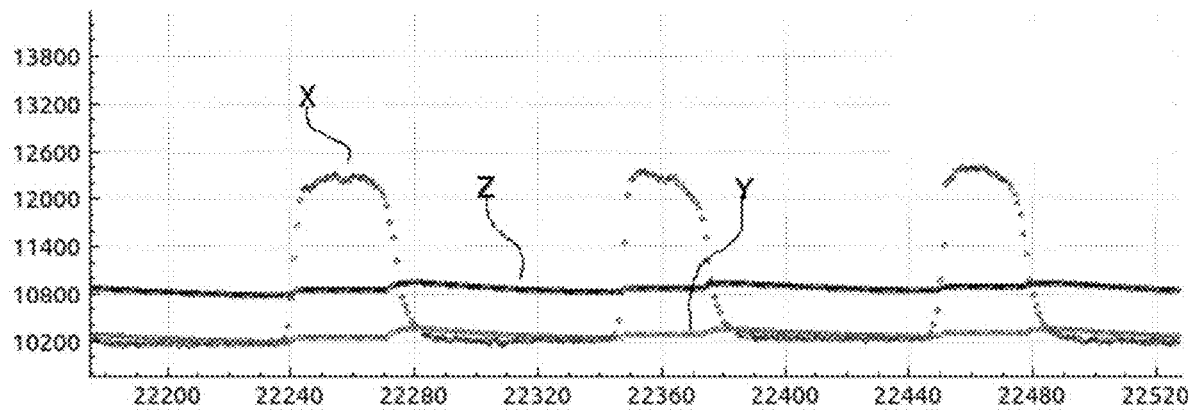
FIG. 1 is a graph showing data used in a determination of eye openness according to one embodiment.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to any embodiment herein shall be an implicit recognition that such detail may or may not be present in any version of any embodiment discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to transitory and non-transitory, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

The present invention generally relates to systems and methods for eye tracking, and the use thereof, in particular, to systems and methods for eye tracking in a wearable device. Wearable devices have risen to prominence in recent years, such devices typically contain at least one display and are commonly used in Virtual Reality (VR) or Augmented Reality (AR) applications.

Eye tracking is the process of determine a person's gaze direction. This is typically done using an image sensor based eye tracking device, where an illuminator projects infrared light onto the eye of a user, and the image sensor captures an image containing a reflection of the infrared light from the eye. From the location of the reflection upon the eye, a gaze direction of the eye can be determined. Eye tracking devices come in various configurations of image sensors, illuminators, and processing structures, as would be readily understood by a person of skill in the art.

Employing eye tracking technology in a wearable device may have certain advantages. For example, it may allow for more natural interaction in a virtual or augmented reality environment.

In one embodiment, a wearable device for wearing on a user's head is provided. The wearable device may include at least one display and an eye tracking device. The eye tracking device may, for example, include at least one image sensor and at least one infrared illuminator, as previously discussed. The image sensor may be any conventional complimentary metal-oxide semiconductor (CMOS) or charge-coupled device (CCD) image sensor containing a plurality of pixels, as would be readily understood by a person of skill in the art.

The eye tracking device may be arranged within the wearable device so as to be in close proximity to a user's eye when the wearable device is worn by the user. A processing unit may be operably coupled with the image sensor(s) and illuminator(s), for processing images captured by the image sensor to determine gaze direction.

As discussed, in some embodiments, the infrared illuminator may project infrared illumination toward the user's eye, and the image sensor captures an image of the user's eye area. The sensor and/or processor may then sum the value or intensity received of all pixels from the captured image (where higher values/intensity are characteristic of closed eyes), resulting in an overall sum X. This is repeated for every image captured by the image sensor. An example of such repeated monitoring is shown in the graph of FIG. 1, which shows sum of intensity (Y-axis) versus time (X-axis). This allows for a binary determination of eye openness, i.e., closed (0) or open (1), at the highest and lowest Y-axis values, but also allows for a more analog determination of various states of openness between closed and open, i.e., quarter open, half open, three-quarters open, and all permutations in-between.

In the example of FIG. 1, the value of X varies over time, having three distinct peaks. These peaks represent increases in the sum of the intensity of pixels of the image sensor which have changed from a previous time (the valleys of FIG. 1), which occurs when a user closes his or her eyelid (e.g., blinking). These peaks can be determined by the processing unit, and thereby relied on to provide an indication to another application that the user is blinking.

The Y data in FIG. 1 is a baseline, which can be adjusted according to various embodiments, and may be different for each individual user. One method of adjusting the baseline Y is to determine a type of low-pass filtered value (for example, a moving average filter value) for images of a particular user's eyes when open.

The Z data in FIG. 1 is a threshold at which the eye is believed to substantially closed, which is compared to the value of X in order to determine if the user is performing a blink. If X exceeds the threshold Z, then it may be determined that the user's eye is performing a closing motion until the value of X returns below the threshold Z. In some embodiments, threshold Z may also be adjusted based on data collected during operation of the methods disclosed herein.

In one embodiment then, the sum of pixels X may be analyzed using the following formulas to determine if a user is blinking:

X=current sum of pixels;
Y=baseline;
A=blink amplitude;
f=blink threshold fraction (in some embodiments, between about ⅛ and about ½);
If X>=Y+f*A then C=0;
If X<Y+f*A then C=1; and
where C=0 is a closed eye, C=1 is an open eye.
To simplify:

$$Z=Y+f*A;$$

if X>=Z then the eye is closed; and
if X<Z then the eye is open.

A is updated with a moving average filter of the value of X only during times when C=0 (the eye is closed).

Figure 1A:
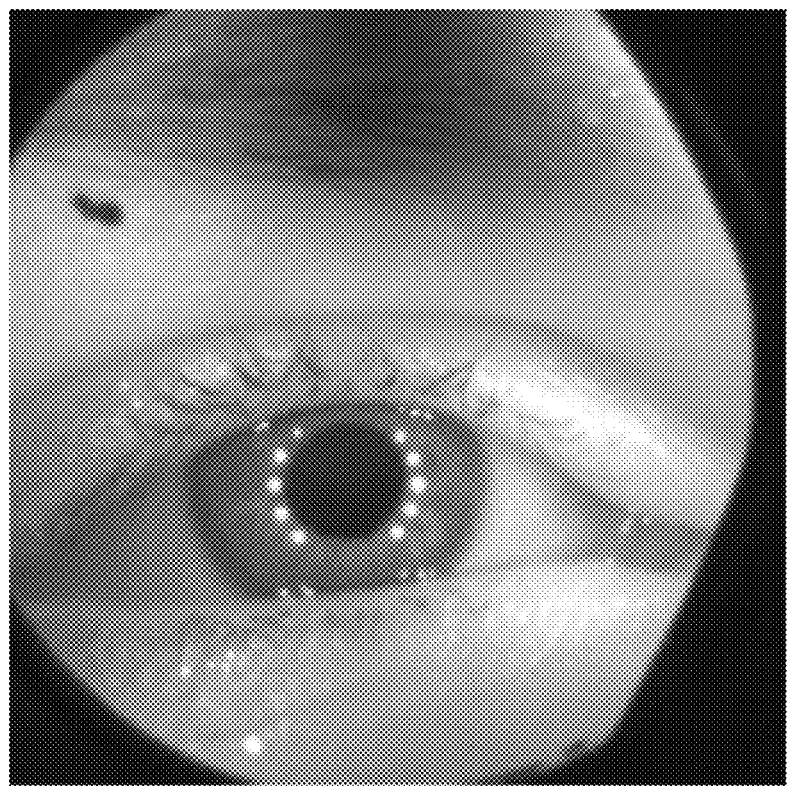
FIG. 1A shows an image of a user's eye having glints indicative of reflections of active illuminators, where the glints are spaced substantially regularly and circularly about the user's pupil.

Y is updated with a moving average filter of the value of X only during times when C=1 (the eye is open). To be more specific, the value of Y will be updated based on the captured image of at least one of the user's eyes indicating the eye is open. The value of Y is set to a predetermined default value at the beginning of the system initialization or at another time. And the value of Y is set to be updated based on each captured image frame of the user's eye(s) or is set to be updated according to a predetermined time sequence and based on the captured image of user's eye(s) at a specific point in time. Preferably, the value of Y is set to a specific value when a predetermined glint pattern is detected, appropriate for the number of illuminators causing potential glints. The predetermined glint pattern indicates the number of the glints meets a predetermined threshold value and the shape of the glints is substantially circular and the locations of the glints are in a predefined region (e.g. the glints are in the vicinity of the pupil.) The distance between the adjacent glints may also be substantially identical. And the glints may be aligned at two sides of the pupil respectively in a circular like pattern). See FIG. 1A for examples of the above characteristics.

Figure 2:
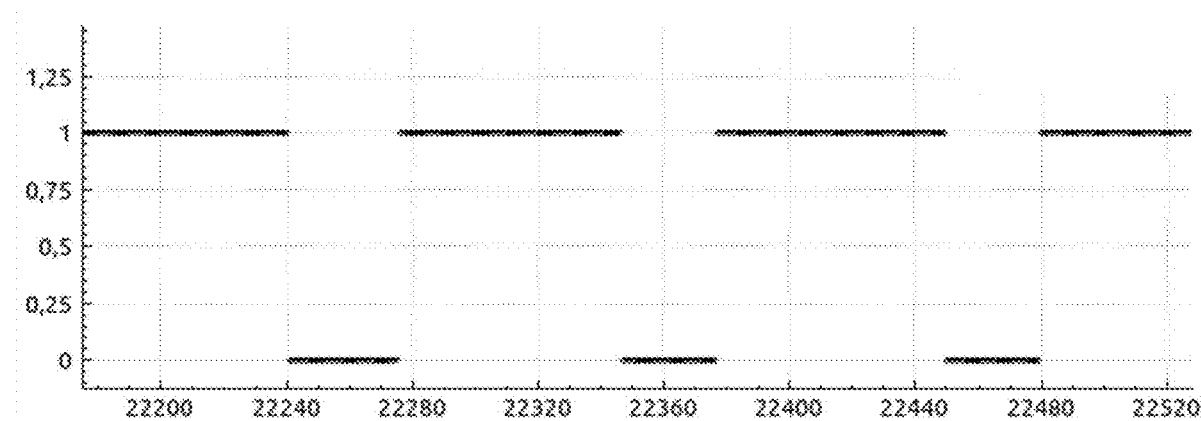
FIG. 2 is a graph showing data used in a determination of eye openness according to one embodiment.

FIG. 2 shows the results of these calculations on the example data of FIG. 1, where the Y-axis represents eye openness (1=open, 0=closed), and the X-axis represents time. By normalizing baseline Y based on the values of X during an open eye conditions (C=1), embodiments herein can account for disturbances in monitoring like head movement, during which the sum of pixels X varies due to external factors such as ambient light, movement in the position of the wearable device, etc.

In another embodiment, rather than the sum of pixels X being used to determine if an eye is open or closed, more particular characteristics of reflections of infrared illumination can be analyzed. For example, in a system where a plurality of infrared illuminators are directed toward a user's eye, such as an eye tracking system, an image captured of the eye may be analyzed to determine if there are any reflections on the eye from the infrared illuminators. If so, the quantity, location, etc. of the reflections can be used to deduce that an eye is open or closed.

For example, consider a case where eight illuminators arranged in a circle are directed toward a user's eye. If an image of the eye reveals glints caused by all eight present illuminators, it can be decided that the user's eye is open. If the image reveals no glints, it can be decided that the user's eye is closed. If the image reveals between 1 and 7 glints caused by the illuminators, it can be decided that the user's eye is in the process of opening or closing. Depending on the embodiment, these interim conditions which occur during opening or closing may be classified as a state of open or closed to make the data binary for analytical purposes In some embodiments, there is also provided a method for determining openness of an eye that can accommodate eyes of different shapes and sizes, and persons whose eyes, when open, may not be as widely open as other users. These methods may be based on the fact that during a blink, no matter the person's normal eye-openness characteristics, a majority of a pupil may be obscured by the eyelid. In contrast, when a user has naturally narrow eyes, or is squinting, despite the overall eyelid position appearing similar to a blink-in-motion, a majority of their pupil will not obscured.

Figure 3:
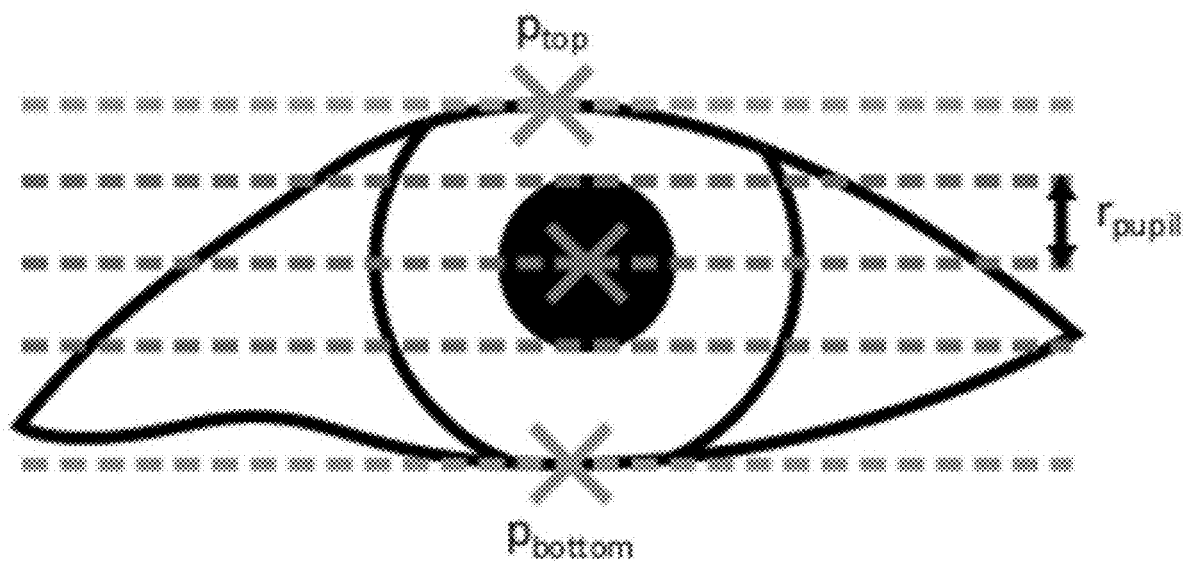
FIGS. 3-7 are images on an eye and various measurement points thereon which are relevant to a method of determining eye openness according to one embodiment.

With regard to these embodiments, various information, as will be described below with reference to FIG. 3, may be relevant:

$p_{top}$=the point where the upper eyelid is the most open;
$p_{botttom}$=the point where the lower eyelid is the most open;
$c_{pupil}$=the pupil center; and
$r_{pupil}$=the pupil radius.

This information may be collected using an image sensor of an eye tracking device, and may be used to estimate the distance between the eyelids of a user. In turn, to accommodate eyes which are naturally narrower, maximum openness can be tracked over time, and methods described herein may be employed to determine whether the eye is open or closed relative to such maximum openness.

Figure 4:
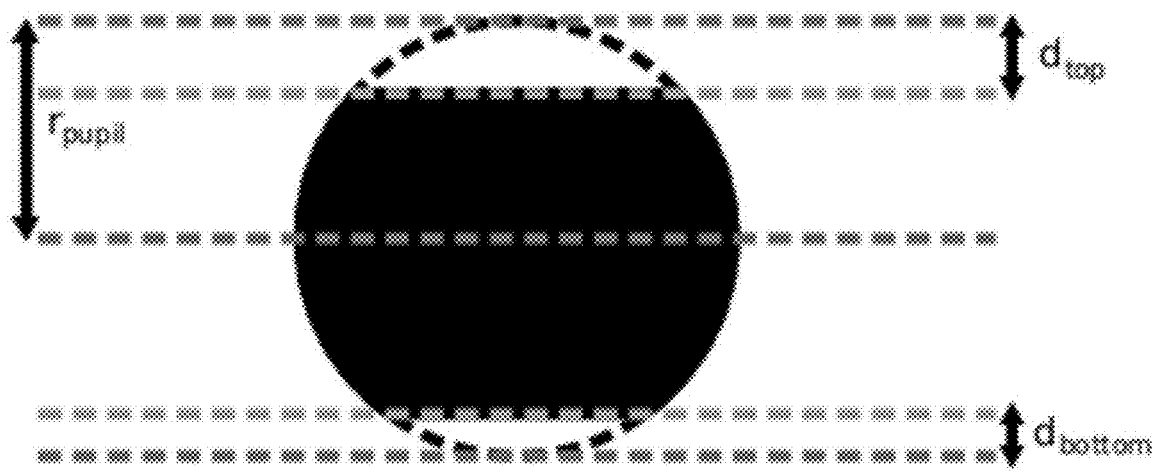
Figure 5:
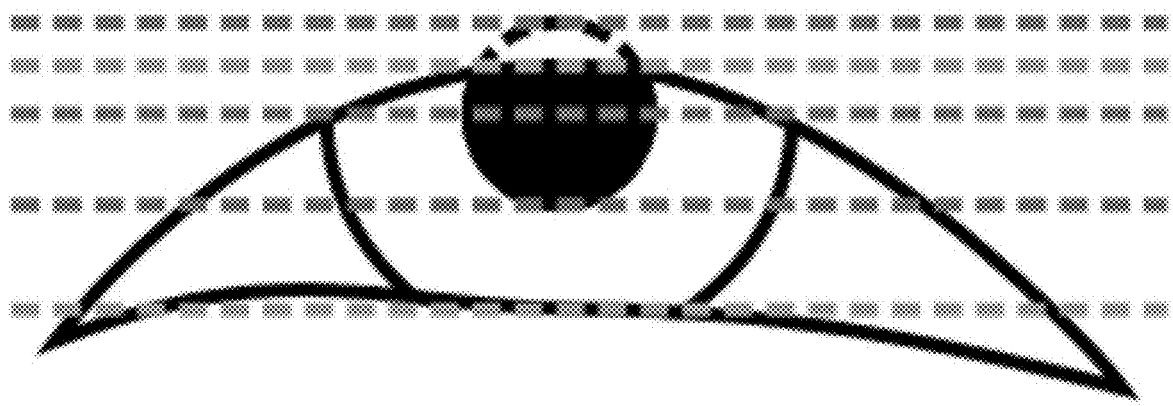
Figure 6:
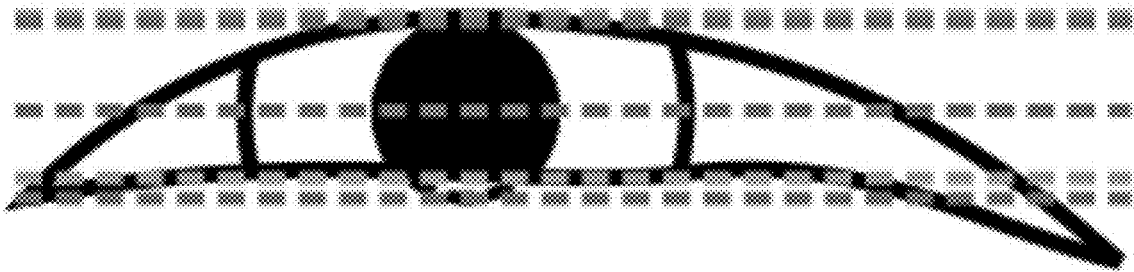
Figure 7:
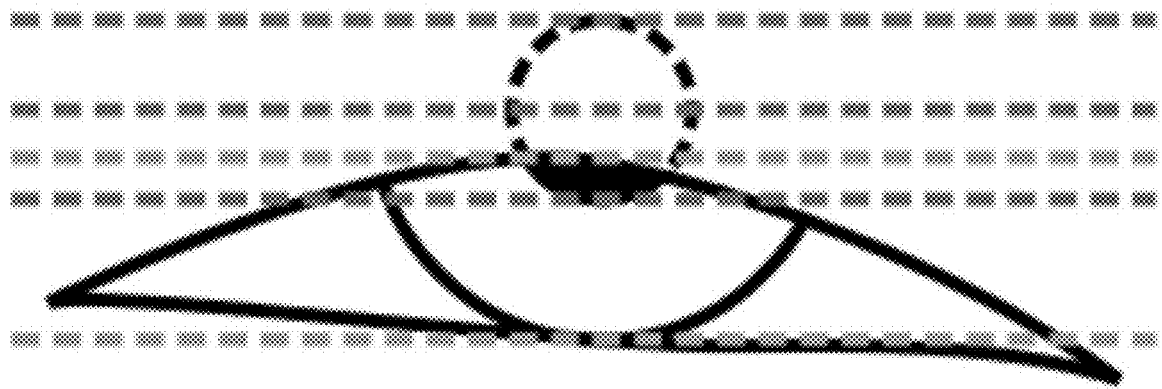

The above information may also be used to determine an estimate the visible fraction of a pupil. With reference to FIG. 4, a method may estimate how much of a pupil is visible, by approximating the eyelid with a horizontal line:

$$\text{area}_{visible} = pi \cdot r_{pupil}^2 - \text{area}_{top} - \text{area}_{bottom};$$

$$\text{area}_{top} = r_{pupil}^2 \cos^{-1}\left(\frac{r_{pupil} - d_{top}}{r_{pupil}}\right) - (r_{pupil} - d_{top})\sqrt{2r_{pupil}d_{top} - d_{top}^2};$$

and $\text{area}_{bottom}$ is computed in the same way from $p_{bottom}$.

With reference to FIGS. 5-8, by tracking the maximum fraction of visible pupil area ($f_{visible,max}$) for a user, eye openness can be computed as:

$$\text{openness} = f_{visible}/f_{visible,max}; \text{ and}$$

$$f_{visible} = \text{area}_{visible}/\text{area}_{pupil}.$$

Alternatively, in a binary determination of eye openness, it may be further advantageous to determine whether the pupil center is located between $d_{top}$ and $d_{bottom}$.

Once the openness, or degree of openness of a user's eye is determined, the information may be used by applications capable of displaying on the wearable device, or other applications. For example in an application that displays an avatar (a computer representation of a person), the eye or eyes on the avatar may be updated to reflect the real life condition of the user's eye or eyes. The application may be running on a local wearable device containing the eye tracking device, or on a remote wearable device in communication with the user's wearable device.

In other embodiments, a specific action may be initiated by a processor or other device upon a determination that the user's eyes are open, closed, or at some state between the two. For example, the eye tracking device may be turned on to a higher power, and/or more active/ready, state if the user's eyes are detected as open. If the user's eyes are detected as closed, the eye tracking device may be turned off or into a lower poser, and/or less active/ready, state. Any other resource, input device, output device, or other device coupled with the processor managing the eye tracking device (or within the tracking device) may also be operated in a like manner based on the determination of eye openness via any of the methods disclosed herein.

Thus, in some embodiments, systems and methods for determining eye openness with an eye tracking device are provided. These embodiments may include determining, for at least a portion of pixels of an image sensor of an eye tracking device, during a first time period when an eye of a user is open, a first sum of intensity of the pixels. In some embodiments, the first sum may be a moving average of intensity of the pixels of the image sensor. The embodiments may also include determining, for the at least portion of pixels of the image sensor of the eye tracking device, during a second time period when the eye of the user is closed, a second sum of intensity of the pixels. The embodiments may further include determining, for the at least portion of pixels of the image sensor of the eye tracking device, during a third time period, a third sum of intensity of the pixels. The embodiments may additionally include determining, with a processor, that upon the third sum exceeding a fourth sum of the first sum plus a threshold amount, that the eye of the user is closed, where the threshold amount is equal to a product of a threshold fraction and a difference between the first sum and the second sum. The threshold fraction may be between about ⅛ and about ½.

In some embodiments, the methods and systems may also include activating an illuminator of the eye tracking device during each of the first time period, the second time period, and the third time period. Also in various embodiments, the first time period may be dynamic and precede the third time period.

In other embodiments, systems and methods for determining eye openness with an eye tracking device are provided. These embodiments may include activating a plurality of illuminators of an eye tracking device, where the plurality of illuminators are directed toward an eye of a user. The embodiments may also include determining, with an image sensor of an eye tracking device, how many reflections of activated illuminators are present on the eye of the user. The embodiments may further include determining, with at least one processor, based on less than a first predefined number of reflections being present, that the eye of the user is closed. In some embodiments, the first predefined number may be one. In various embodiments, the first predefined number may be selected from a group consisting of all integers between zero and a total number of the plurality of illuminators. In various embodiments, the methods and systems may also include determining, with the at least one processor, based on the number of reflections being more than zero, but less than a total number of the plurality of illuminators, that the eye of the user is in a process of opening or closing.

In other embodiments, systems and methods for determining eye openness with an eye tracking device are provided. These embodiments may include receiving, at one or more processors, an image of an eye of a user from an image sensor of an eye tracking device. The embodiments may also include determining, with the one or more processors, based on the image of the eye, a radius of the pupil. The embodiments may further include determining, with the one or more processors, based on the radius of the pupil, a total area of the pupil. The embodiments may additionally include determining, with the one or more processors, based on the image of the eye and the radius of the pupil, an amount of the total area of the pupil which is not obscured by either eyelid. The embodiments may moreover include determining, with the one or more processors, based on the amount of the total area of the pupil which is not obscured by the eyelid and the total area of the pupil, whether the eye of the user is closed.

Thus, in some embodiments, when the total area of the pupil which is not obscured is greater than a remainder of the pupil, the eye of the user is open. In these or other embodiments, when the total area of the pupil which is not obscured is less than a remainder of the pupil, the eye of the user is closed.

In some embodiments, the systems and methods may further include determining, with the one or more processors, based on the image of the eye, that a center of the pupil is obscured by either eyelid, and determining, with the one or more processors, based on the center of the pupil being obscured by either eyelid, that the eye of the user is closed. In these or other embodiments, the systems and methods may further include determining, with the one or more processors, based on the image of the eye, a maximum openness over time between either eyelids, and determining, with the one or more processors, whether the eye of the user is closed based on the maximum openness over time. Determining whether the eye of the user is closed based on the maximum openness over time may include determining, based on the image of the eye, that an openness of the eye is less than a predefined proportion of the maximum openness over time.

In the above or other embodiments, there may also be provided a system and method for instructing a user to appropriately position a wearable device upon their head, where said wearable device contains an eye tracking device. The wearable device may be in the form of a VR or AR headset having at least one display. The wearable device may include an eye tracking device having at least one image sensor and at least one infrared illuminator, where the image sensor may be arranged so as to be able to capture and image of at least a portion of a wearer's eye, and the infrared illuminator may be arranged to project infrared illumination onto a wearer's eye.

According to such embodiments, an application is executed by a processor, causing items to be displayed on the display of the wearable device. These items may be graphical guides for a user wearing the wearable device, so as to assist the user in positioning the wearable device upon the user's head in a manner so as to allow for functional eye tracking by the eye tracking device.

Figure 8:
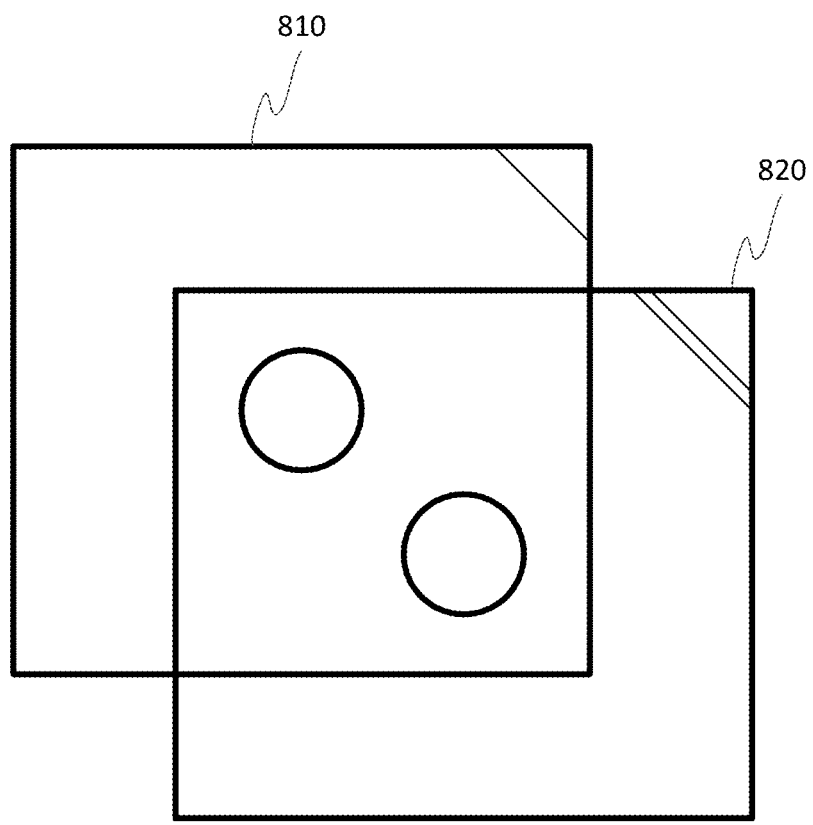
FIG. 8 shows two visual guides which represent the position of an image sensor and the user's eye relative thereto, and which may be presented in some embodiments to assist a user in positioning an eye tracking device or a wearable device which includes an eye tracking device.

As shown in FIG. 8, these graphical guides may be in the form of a first graphical guide 810 and a second graphical guide 820. First graphical guide 810 may represent an approximation of a lens incorporated into an image sensor in the eye tracking device, and second graphical guide 820 may represent an approximation of user's eye as detected by the eye tracking device.

In practice, when second graphical guide 820 is overlaid upon first graphical guide 810 it provides the user with a visual representation of the location of their eye or eyes relative to the lens of an image sensor imaging their eyes.

For eye tracking to function correctly, it is advantageous that the user's eye or eyes be located as close to the center of the lens as possible. As the user repositions or moves the wearable device, the position of their eye or eyes relative to the lens will change, and therefore so will second graphical guide 820 relative to first graphical guide 810.

Either or both of graphical guides 810, 820 may change color to indicate the suitability of the current position of the user's eye or eyes for eye tracking. For example the color green may be used to indicate an very correlated position, while the color red may indicate an inadequately correlated position. Other colors, for example orange, may be used to indicate an adequately correlated position (i.e., not perfectly correlated, but sufficient for usable eye tracking).

In some embodiments, text may also be placed upon the display to instruct the user as to how to reposition the wearable device. Or text may be adapted in response to the currently determined position of the user's eye or eyes.

The position of the wearable device may be adjusted by moving the entire unit, or the two lenses may be adjusted relative to each other. This may be performed by a mechanical means, such as rotating a knob connected to a gear to mechanically slide the two lenses closer together or further apart, or via electronic means controlling a motor or the like.

In some embodiments, the position of the lenses of the wearable device relative to the user's eyes may be determined from automated processes described below and thereafter optimized by the user with assistance/instruction from the automated processes. In some of these embodiments, the automated processes may also even automatically optimize the position after determining the position of the lens relative to the user's eyes.

One such system may include a wearable device and one or more processors. The system and/or the user may perform various methods, and/or execute various methods stored on machine readable mediums. In some embodiments, one, more, or all of the processors will be disposed within the wearable device. In these embodiments, one, more, or all of the processors will be disposed within the eye tracking device of the wearable device. In some embodiments, one, more, or all of the processors will be disposed within a separate but communicatively coupled computing device (for example, a mobile device, a tablet, a notebook, a laptop, a desktop, or a remote/cloud computing device).

The wearable device may include a display, at least one lens movably disposed in front of the display, and an eye tracking device including at least one illuminator and at least on image sensor. The display may be an LCD and/or LED display typical of VR headsets, display modules such as retinal scan displays and/or retinal projectors, and the lenses may be Fresnel and/or other lens intended to assist the wearable device in providing a three-dimensional immersive effect for the user viewing the display. In some embodiments, multiple Fresnel or other lenses in series may be combined into a lens stack and employed in lieu of a single lens. While the distance between the display and the lenses may be fixed in many embodiments, the distance between the lenses and the user's eyes may be adjustable in the wearable device. Optimization of this distance may improve presentation of the display to the user such that an improved three-dimensional immersive effect is provided to the user.

The eye tracking device may be one known in the art capable of determining various data related to a user's eyes, including data indicative of the gaze direction, as well as the location of the eye, or some portion thereof, relative to the image sensors of the eye tracking device (or some other component whose position is fixed relative to the image sensors).

The one or more processors may be configured to receive data from the eye tracking device, and determine, based at least on the data, a first position of at least one eye of a user wearing the wearable device, where the position is relative to a second position which is fixed with respect to the at least one lens. As described above, data from the eye tracking device may be evaluated by the processors to determine the first position of an eye of the user. In other embodiments however, the eye tracking device may determine the first position of the eye of the user, and report it directly to the processor.

In some embodiments, the data from the eye tracking device may be data representative from a single point in time during which the image sensor of the eye tracking device captures a single image frame. In other embodiments, the data from the eye tracking device may be data representative of multiple consecutive image frames, while in yet other embodiments, multiple image frames taken at differing or consistent intervals over time. In any of the above scenarios, the data may be used to determine the location of the eye of the user. Embodiments which use multiple images to arrive at mean/average data may be advantageous to ensure accounting for small fluctuations due to fluctuations/error in the eye tracking device's measurements, small movements of the wearable device relative to the user's eye during normal use, and/or etc.

The first position may be any consistently located position on a user's eye. Merely by way of example, the first position may represent the location of a pupil of one eye of the user. In another example, the first position may represent a location of a cornea spherical region of one eye of the user. Any other consistent characteristic location on a user's eye may also be used as the location of the first position.

The first and second positions may have any one or more of three axial components. Merely by way of example, either position may have an X-axis position, a Y-axis position, and a Z-axis position. In some embodiments, the X and Y-axes may be coplanar to the display (and the lenses disposed in front of the display), while the Z-axis may be perpendicular to the X and Y-axes (i.e., toward and away from the user as they view the display; also referred to as the lens relief direction).

In either case, the first position of the eye of the user may be determined relative to a fixed second position. The fixed position may be located at any consistent point in space, and may for example be, the position of any component discussed herein, or any position fixed relative to such components. In some embodiments, the second position may be fixed at some location between two lenses of the wearable device. In some augmented reality or other types of display-less headsets, a light-guide or waveguide may be employed to deliver video displays to the user. In these embodiments, the second position may be a fixed position at some point on a light-guide or waveguide, or relative (possibly in-between) multiple light-guides or waveguides configured to deliver video projections to one or both eyes of the user.

The one or more processors may also be configured to determine a distance between the first position and the second position. Because the first position is determined relative to the second position, the distance is determinable by the processor and/or eye tracking device. As noted above, both the first position and the second position may have X, Y, and Z-axes, and therefore the distance between the two positions may be determined to have vectors in each of these directions.

Once the distance is determined, it is compared to one or more threshold values. The threshold values may represent a minimum distance for optimal positioning of the lens with respect to the user's eyes, a maximum distance for optimal positioning of the lens with respect to the user's eyes, or both. In any given embodiment, all or some of the above described directional vectors of the distance (i.e., x, y, and/or z-axes) may be compared to all or some of directional vectors of a threshold value (i.e., x, y, and/or z-axes). Therefore, merely by way of example, only the z-axis vector of the distance may be compared to the z-axis vector of a threshold value or values to determine if the lens is too far or too close to the user's eye. In other embodiments, the x and/or y-axes will also be taken into account.

Additionally, in some embodiments multiple thresholds may be employed. For example, a high limit threshold may represent a maximum distance for which the methods herein define an optimal lens position relative to the user's eye, while a low limit threshold may represent a minimum distance for which the methods herein define an optimal lens position relative to the user's eye.

In some embodiments, the threshold values may be dynamic, and change over time based on other variables. Merely by way of example, the processors may be informed of, or able to analyze, content being provided to the user on the display and determined that a different threshold value or values are optimum during such time (for example, possibly different thresholds representative of different relief distances necessary for certain content), visual characteristics (i.e., brightness, contrast, percentage of display pixels changing, etc.), eyewear presence (i.e., glasses), and/or other factors may prompt a changing of threshold values.

For example, if the distance is greater than a first value, methods of various embodiments may cause information to be presented to the user indicating that the one or more lens should be moved to a more optimal position. This information may be audibly, visually, or tactilely presented. In various examples: the method may cause content to be presented on the display which informs the user that the lenses are too close, or too far from the user's eye. The content may also inform the user how to manually cause the lens to be repositioned in light thereof. For example, the user wearable device may have a control on it to mechanically or electro-mechanically move the lens as described. The content displayed may instruct the user on the location and particulars of such control. In some embodiments, audible information may be presented to the user via a speaker, etc. In some embodiment tactile feedback be presented to the user, perhaps by intermittent/pulsed operation of an automatic electro-mechanical movement system which can reposition the lens without manual user input.

Thus, in some embodiments, an electro-mechanical movement system may be provided to automatically reposition the lens with respect to the user's eyes based on the distance determination made earlier (and thereafter compared to the threshold values). This automatic repositioning may occur upon completion of the comparison of the determined distance with the threshold(s). As with the determination of the distance and comparison to the thresholds, this process may repeat automatically over time, and/or at the direction of the user (by instruction from the user to the processors, etc.). In some embodiments, automatic electro-mechanical movements systems may also be present to move each of two lenses in the wearable device closer to, or away from, each other, potentially in the x-axis direction (i.e., left-right with respect to the user). Such automatic movement systems may be employed to implement other embodiments of the invention such as those discussed above to account for changes needed to eye-to-eye or inter-pupillary distance.

Figure 9:
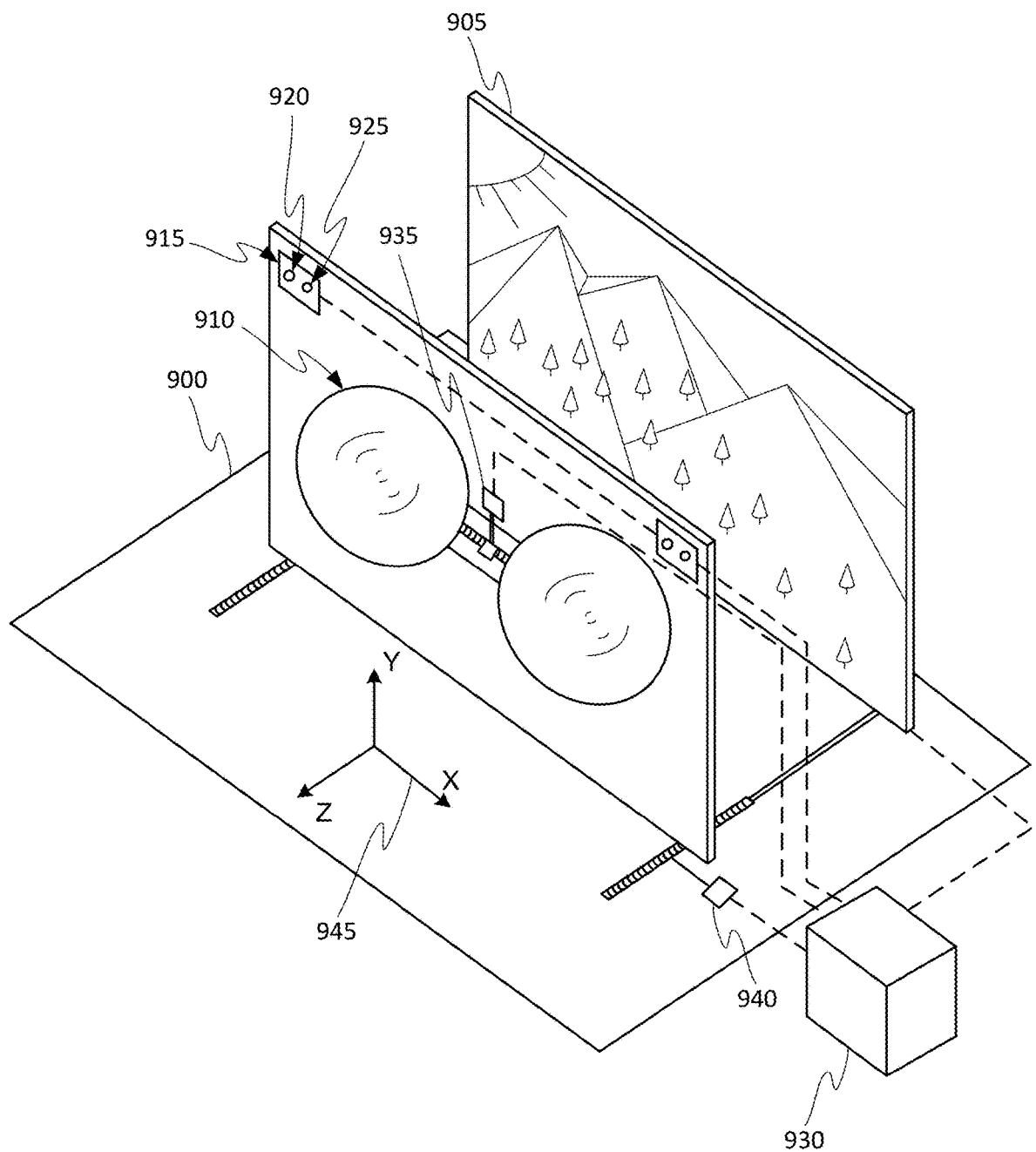
FIG. 9 shows a wearable device of one embodiment of the invention capable of detecting the position of the lenses therein, and at least assisting the user in adjusting the same.

FIG. 9 shows a wearable device 900 having the components described above. Wearable device 900 includes a display 905 (some embodiments may have a separate display for each eye), two lenses 910, and an eye tracking device 915. Each portion of the eye tracking device 915 may have at least one illuminator 920 and at least one image sensor 925. Processor 930 may receive data from, and issue instructions to, the components of device 900 as described above.

A first electro-mechanical movement system 935 may provide a means for lenses 910 to be moved relative to each other, while a second electro-mechanical movement system 940 may provide a means for lenses 910 to me moved relative to the user's eyes (not shown, but would be present on left side of device 900 during use). In some embodiments, both movement systems 935, 940 may only be manually operable by the user (i.e., via knob, etc.). Orientation axes 945 in the X, Y, and Z direction as discussed above are also shown.

Figure 10:
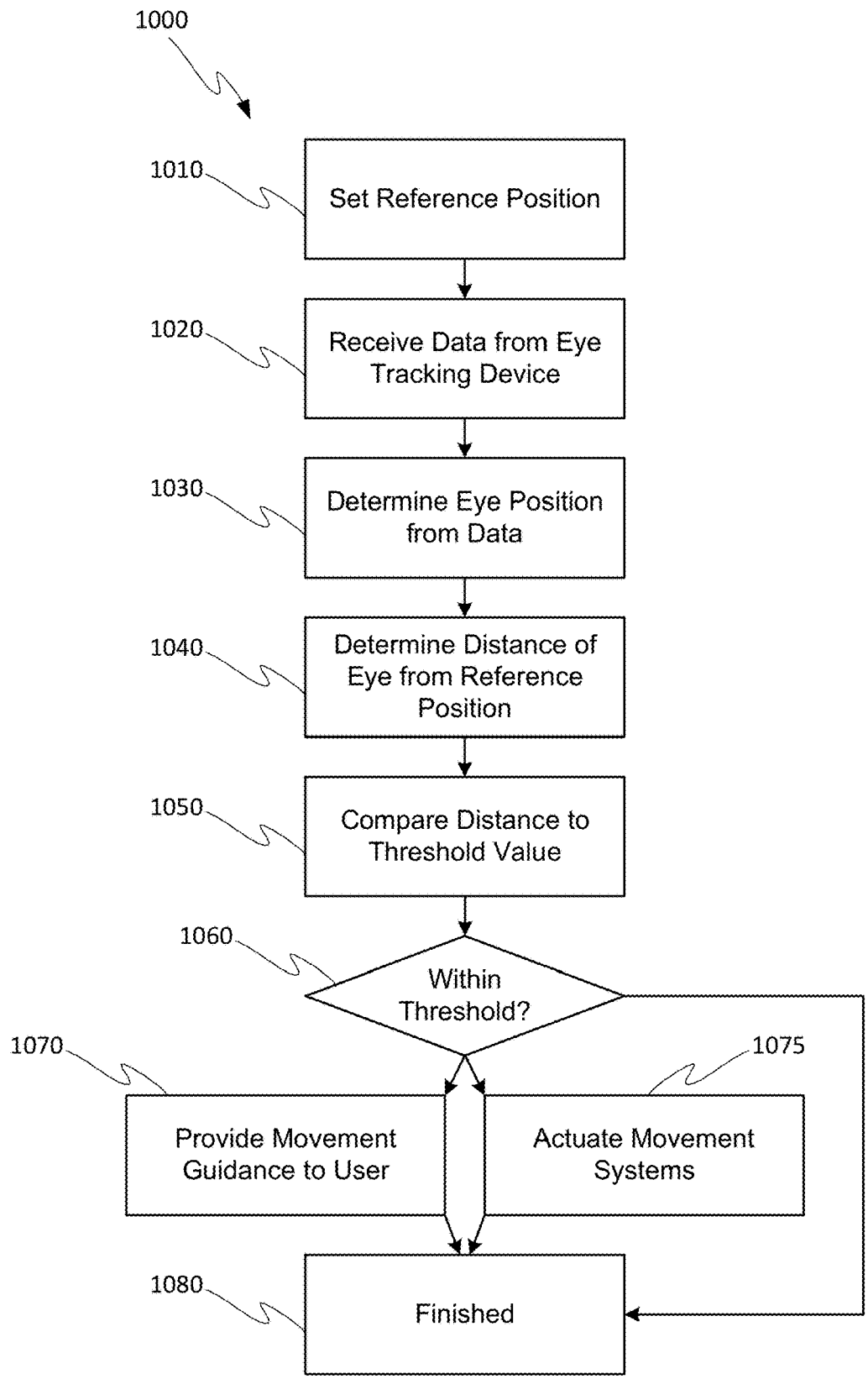
FIG. 10 shows a block diagram of one method embodiment of the invention for detecting and adjusting the position of lenses of a wearable device.

FIG. 10 is a block diagram of a method 1000 as described for adjusting the location of lenses in a wearable device. At block 1010, a reference position is determined or otherwise identified, perhaps as pre-defined. At block 1020, data is received from the eye tracking device.

At block 1030, an eye position is determined from the data. At block 1040, the distance from the reference position to the eye position is determined. At block 1050 the distance is compared to a threshold value.

At block 1060, if the distance is within the threshold value, then method 1000 ends at block 1080. If the distance is not within the threshold value at block 1060, then movement guidance is provided to the user at block 1070, or movement systems are automatically actuated at block 1075 to bring the distance within the threshold. Method 1000 may repeat whenever the system is reset, between application execution on the wearable device, or at regular or irregular intervals, in order to ensure optimal lens distance.

Figure 11:
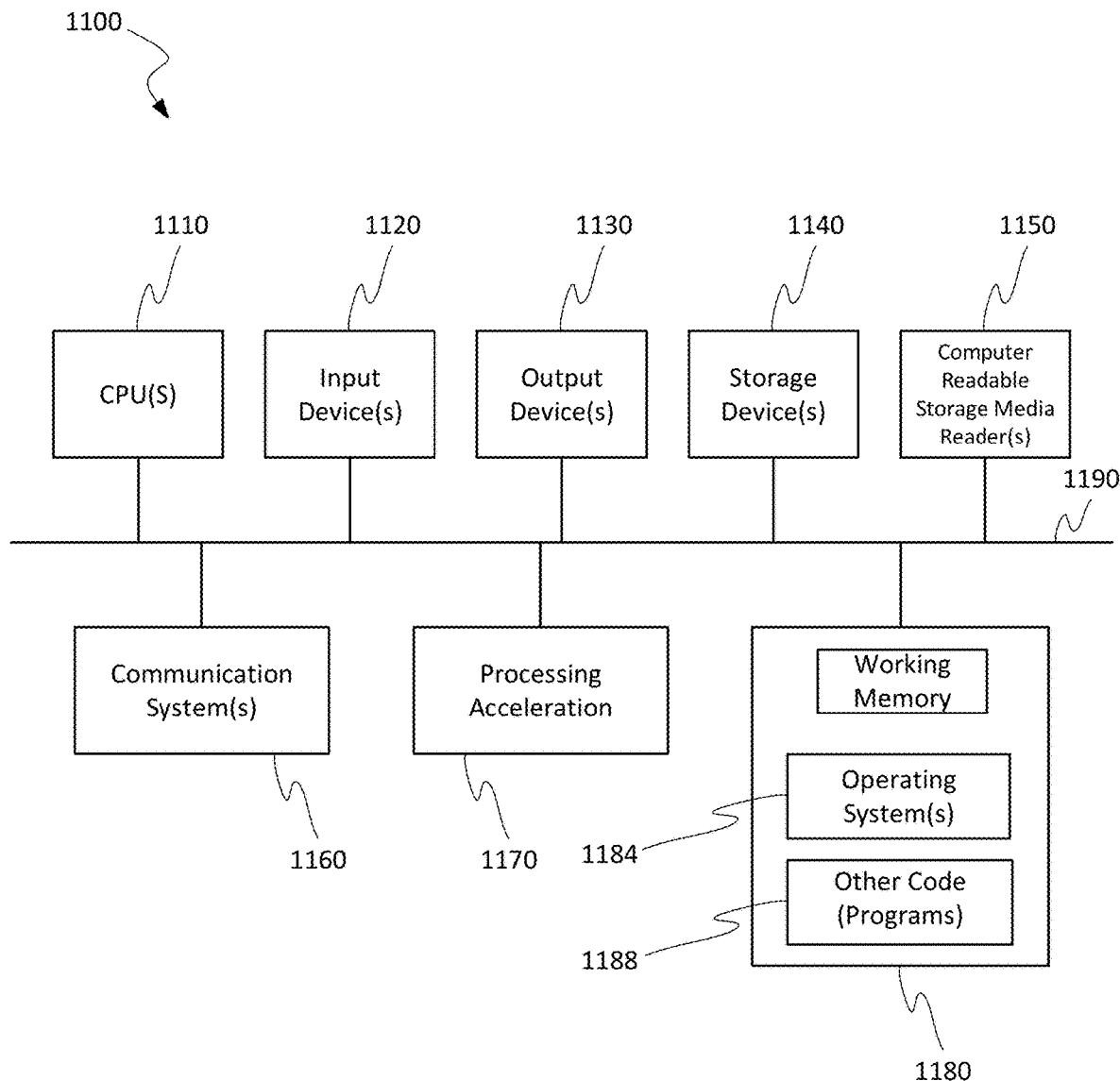
FIG. 11 is a block diagram of a specialized computer system capable of being used in at least some portion of the apparatuses or systems of the present invention, or implementing at least some portion of the methods of the present invention.

FIG. 11 is a block diagram illustrating a specialized computer system 1100 in which embodiments of the present invention may be implemented. This example illustrates specialized computer system 1100 such as may be used, in whole, in part, or with various modifications, to provide the functions of display 905, eye tracking devices 915, processors 930, movement systems 935, 940, and/or other components of the invention such as those discussed above. For example, various functions of processors 930 may be controlled by specialized computer system 1100, including, merely by way of example, determining distances from eye features to a reference point, comparing distances to predefined thresholds, etc.

Specialized computer system 1100 is shown comprising hardware elements that may be electrically coupled via a bus 1190. The hardware elements may include one or more central processing units 1110, one or more input devices 1120 (e.g., a mouse, a keyboard, a touchpad, an eye tracking device, etc.), and one or more output devices 1130 (e.g., a display device, a printer, etc.). Specialized computer system 1100 may also include one or more storage device 1140. By way of example, storage device(s) 1140 may be disk drives, optical storage devices, solid-state storage device such as a random access memory ("RAM") and/or a read-only memory ("ROM"), which can be programmable, flash-updateable and/or the like.

Specialized computer system 1100 may additionally include a computer-readable storage media reader 1150, a communications system 1160 (e.g., a modem, a network card (wireless or wired), an infra-red communication device, Bluetooth™ device, cellular communication device, etc.), and working memory 1180, which may include RAM and ROM devices as described above. In some embodiments, specialized computer system 1100 may also include a processing acceleration unit 1170, which can include a digital signal processor, a special-purpose processor and/or the like.

Computer-readable storage media reader 1150 can further be connected to a computer-readable storage medium, together (and, optionally, in combination with storage device(s) 1140) comprehensively representing remote, local, fixed, and/or removable storage devices plus storage media for temporarily and/or more permanently containing computer-readable information. Communications system 1160 may permit data to be exchanged with a network, system, computer and/or other component described above.

Specialized computer system 1100 may also comprise software elements, shown as being currently located within a working memory 1180, including an operating system 1184 and/or other code 1188. It should be appreciated that alternate embodiments of specialized computer system 1100 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of specialized computer system 1100 may include code 1188 for implementing any or all of the function of the various elements of the architecture as described herein. For example, software, stored on and/or executed by a specialized computer system such as specialized computer system 1100, can provide the functions of display 905, eye tracking devices 915, movement systems 935, 940, processors 930, and/or other components of the invention such as those discussed above. Methods implementable by software on some of these components have been discussed above in more detail.

The invention has now been described in detail for the purposes of clarity and understanding. However, it will be appreciated that certain changes and modifications may be practiced within the scope of the appended claims.

What is claimed is:

1. A system for adjusting a position of a lens in a wearable device, comprising:
   a wearable device including:
      a display;
      two lenses movably disposed in front of the display;
         wherein the two lenses being movably disposed in front of the display comprises:
         a first lens being movably disposed relative to a second lens; and
         the first lens and the second lens being movably disposed relative to at least one eye of the user wearing the wearable device,
      and
      an eye tracking device comprising at least one illuminator and at least on image sensor; and
   one or more processors configured to:
      receive data from the eye tracking device;
      determine, based at least on the data, a first position of at least one eye of a user wearing the wearable device, wherein the position is relative to a second position which is fixed with respect to the lenses, and wherein the second position comprises a location between the first lens and the second lens;
      determine a distance between the first position and the second position; and
      if the distance is greater than a first value, cause information to be presented to the user indicating that the first lens and the second lenses should be moved to a more optimal position.

2. The system for adjusting a position of a lens in a wearable device of claim 1, wherein:
   at least one of the one or more processors is disposed in the wearable device.

3. The system for adjusting a position of a lens in a wearable device of claim 1, wherein the first position of at least one eye of the user comprises:
   a location of a pupil of one eye of the user.

4. The system for adjusting a position of a lens in a wearable device of claim 1, wherein the first position of at least one eye of the user comprises:
   a location of a cornea spherical region of one eye of the user.

5. The system for adjusting a position of a lens in a wearable device of claim 1, wherein the data from the eye tracking device comprises:
   data representative of a single image frame.

6. The system for adjusting a position of a lens in a wearable device of claim 1, wherein the data from the eye tracking device comprises:
   data representative of consecutive image frames.

7. The system for adjusting a position of a lens in a wearable device of claim 1, wherein the data from the eye tracking device comprises:
   data representative of a plurality of image frames over a period of time.

8. The system for adjusting a position of a lens in a wearable device of claim 1, wherein the distance comprises:
   an x-axis component;
   a y-axis component; and
   a z-axis component, wherein:
   the x-axis component and the y-axis component are in a plane parallel with the display; and
   the z-axis component are in a plane perpendicular to the display.

9. The system for adjusting a position of a lens in a wearable device of claim 8, wherein the distance being greater than the first value comprises:
   the z-axis component being greater than a second value.

10. A method for adjusting a position of a lens in a wearable device, the method comprising:
    receiving data from an eye tracking device in a wearable device including a display and two lenses movably disposed in front of the display;
    determining, based at least on the data, a first position of at least one eye of a user wearing the wearable device, wherein the position is relative to a second position which is fixed with respect to a first lens and a second lens, and wherein the second position comprises a location between the first lens and the second lens, wherein the first lens and the second lens are movably disposed in front of the display and wherein:
    the first lens is movably disposed relative to the second lens; and
    the first lens and the second lens are movably disposed relative to at least one eye of the user wearing the wearable device;
    determining a distance between the first position and the second position; and
    if the distance is greater than a first value or less than a second value, causing information to be presented to the user indicating that the first lens and the second lens should be moved to a more optimal position.

11. The method for adjusting a position of a lens in a wearable device of claim 10, wherein:
    the first value comprises:
      a first x-axis component;
      a first y-axis component; and
      a first z-axis component;
    the second value comprises:
      a second x-axis component;
      a second y-axis component; and
      a second z-axis component;
    the distance comprises:
      a third x-axis component;
      a third y-axis component; and
      a third z-axis component.

12. The method for adjusting a position of a lens in a wearable device of claim 11, wherein the distance being greater than a first value comprises:
    the third x-axis component being greater than the first x-axis component;
    the third y-axis component being greater than the first y-axis component; and
    the third z-axis component being greater than the first z-axis component.

13. The method for adjusting a position of a lens in a wearable device of claim 11, wherein the distance being less than a second value comprises:
    the third x-axis component being less than the second x-axis component;
    the third y-axis component being less than the second y-axis component; and
    the third z-axis component being less than the second z-axis component.

14. The method for adjusting a position of a lens in a wearable device of claim 10, wherein the first value or the second value comprise:
    a dynamic value, wherein the dynamic value is based at least in part on characteristics of at least one eye of the user or whether the user is wearing glasses.

15. A non-transitory machine readable medium having instructions stored thereon for adjusting a position of a lens in a wearable device, wherein the instructions are executable by one or more processors for at least:
    receiving data from an eye tracking device in a wearable device including a display and two lenses movably disposed in front of the display, wherein the two lenses being movably disposed in front of the display comprises:
    a first lens being movably disposed relative to a second lens; and
    the first lens and the second lens being movably disposed relative to at least one eye of the user wearing the wearable device;
    determining, based at least on the data, a first position of at least one eye of a user wearing the wearable device, wherein the position is relative to a second position which is fixed with respect to the lenses, and wherein the second position comprises a location between the first lens and the second lens;
    determining a distance between the first position and the second position; and
    if the distance is greater than a first value or less than a second value, causing the at least one lens to be moved until the distance is less than the first value or greater than the second value.

16. The non-transitory machine readable medium of claim 15, wherein the first lens being movably disposed relative to the second lens comprises: the first lens or the second lens being movably disposed such that it is capable of moving toward or away the other of the first lens or the second lens.

17. The non-transitory machine readable medium of claim 15, wherein the first lens and the second lens being movably disposed relative to at least one eye of the user wearing the wearable device comprises: the first lens and the second lens being movably disposed such that they are capable of moving toward or away the at least one eye of the user wearing the wearable device.

18. The non-transitory machine readable medium of claim 17, wherein causing the at least one lens to be moved until the distance is less than the first value and greater than the second value comprises:
    causing a movement device coupled with the first lens and the second lens to engage until the distance is less than the first value or greater than the second value.

* * * * *